(12) United States Patent
Teichman et al.

(10) Patent No.: US 9,504,531 B2
(45) Date of Patent: Nov. 29, 2016

(54) METHOD AND APPARATUS FOR IMAGE-BASED NAVIGATION

(71) Applicant: Medtronic Navigation, Inc., Louisville, CO (US)

(72) Inventors: Robert Teichman, Lafayette, CO (US); Eric Potts, Indianapolis, IN (US); Robert J. Reddy, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 14/492,728

(22) Filed: Sep. 22, 2014

(65) Prior Publication Data

US 2015/0010220 A1 Jan. 8, 2015

Related U.S. Application Data

(63) Continuation of application No. 12/771,576, filed on Apr. 30, 2010, now Pat. No. 8,842,893.

(51) Int. Cl.
*G06K 9/62* (2006.01)
*G06T 19/00* (2011.01)
*A61B 19/00* (2006.01)

(52) U.S. Cl.
CPC ........... *A61B 19/5244* (2013.01); *A61B 34/20* (2016.02); *G06K 9/6202* (2013.01); *G06T 19/006* (2013.01); *A61B 2034/102* (2016.02); *A61B 2034/107* (2016.02); *A61B 2034/2051* (2016.02)

(58) Field of Classification Search
None
See application file for complete search history.

(56) References Cited

U.S. PATENT DOCUMENTS

| | | | |
|---|---|---|---|
| 5,592,939 | A | 1/1997 | Martinelli |
| 5,913,820 | A | 6/1999 | Bladen et al. |
| 5,983,126 | A | 11/1999 | Wittkampf |
| 6,132,437 | A | 10/2000 | Omurtag et al. |
| 6,474,341 | B1 | 11/2002 | Hunter et al. |
| 6,747,539 | B1 | 6/2004 | Martinelli |
| 6,940,941 | B2 | 9/2005 | Gregerson et al. |
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |

(Continued)

FOREIGN PATENT DOCUMENTS

| | | |
|---|---|---|
| EP | 2563258 A1 | 3/2013 |
| WO | WO-2004017836 A2 | 3/2004 |

(Continued)

OTHER PUBLICATIONS

"AxiEM Electromagetic Navigation," tri-fold brochure, Medtronic Navigation (2005) 2 pages.

(Continued)

*Primary Examiner* — Michelle Entezari
(74) *Attorney, Agent, or Firm* — Harness, Dickey

(57) ABSTRACT

A system and method for a procedure that can be performed on any appropriate subject. Procedures can include assembling any appropriate work piece or installing members into a work piece, such as an airframe, autoframe, etc. Regardless of the subject, generally the procedure can have a selected result that is efficacious. The efficacious result may be the desired or best result for the procedure. The system and method can be used in confirming a selected result that can be efficacious.

18 Claims, 10 Drawing Sheets

(56) References Cited

U.S. PATENT DOCUMENTS

| | | |
|---|---|---|
| 7,235,076 B2 | 6/2007 | Pacheco |
| 7,383,164 B2 * | 6/2008 | Aram ................ A61F 2/30942 600/300 |
| 7,623,902 B2 | 11/2009 | Pacheco |
| 7,751,865 B2 | 7/2010 | Jascob et al. |
| 7,797,032 B2 | 9/2010 | Martinelli et al. |
| 7,873,234 B2 * | 1/2011 | Boyden ................ G01R 33/565 382/131 |
| 7,986,836 B2 | 7/2011 | Von Berg et al. |
| 8,073,216 B2 | 12/2011 | Dawant et al. |
| 8,126,234 B1 | 2/2012 | Edwards et al. |
| 8,189,889 B2 * | 5/2012 | Pearlstein ............. A61B 6/583 382/128 |
| 8,280,189 B2 | 10/2012 | Bar-Tal et al. |
| 8,423,135 B2 * | 4/2013 | Doerr ..................... A61N 1/37 607/4 |
| 8,842,893 B2 | 9/2014 | Teichman et al. |
| 9,135,686 B2 * | 9/2015 | Boyden .................. G06T 5/006 |
| 2001/0036245 A1 | 11/2001 | Kienzle et al. |
| 2002/0039443 A1 | 4/2002 | Sakamoto |
| 2003/0117135 A1 | 6/2003 | Martinelli et al. |
| 2003/0191394 A1 * | 10/2003 | Simon .................... A61B 6/481 600/473 |
| 2004/0017836 A1 | 1/2004 | Buda et al. |
| 2004/0116803 A1 | 6/2004 | Jascob et al. |
| 2004/0171924 A1 | 9/2004 | Mire et al. |
| 2004/0171930 A1 * | 9/2004 | Grimm ............. A61B 17/1703 600/424 |
| 2004/0184645 A1 | 9/2004 | Muller |
| 2004/0199072 A1 | 10/2004 | Sprouse et al. |
| 2005/0021043 A1 | 1/2005 | Jansen et al. |
| 2005/0085720 A1 | 4/2005 | Jascob et al. |
| 2005/0203384 A1 | 9/2005 | Sati et al. |
| 2006/0002630 A1 * | 1/2006 | Fu ............................ G06K 9/32 382/294 |
| 2006/0036323 A1 | 2/2006 | Carl et al. |
| 2006/0182349 A1 * | 8/2006 | Valadez ................ G06T 7/2053 382/221 |
| 2006/0258938 A1 * | 11/2006 | Hoffman ............. A61B 1/00193 600/424 |
| 2007/0173744 A1 | 7/2007 | Lai et al. |
| 2007/0232960 A1 | 10/2007 | Pacheco |
| 2007/0265518 A1 | 11/2007 | Boese et al. |
| 2007/0276383 A1 | 11/2007 | Rayhack |
| 2008/0154120 A1 | 6/2008 | von Jako et al. |
| 2008/0177203 A1 | 7/2008 | von Jako |
| 2008/0183030 A1 * | 7/2008 | Shiri ....................... A63F 13/10 600/27 |
| 2008/0200794 A1 | 8/2008 | Teichman et al. |
| 2008/0243142 A1 * | 10/2008 | Gildenberg ............ A61B 19/52 606/130 |
| 2008/0300477 A1 | 12/2008 | Lloyd et al. |
| 2009/0154770 A1 | 6/2009 | Akiyama |
| 2009/0177452 A1 * | 7/2009 | Ullrich ................. G09B 23/285 703/11 |
| 2010/0138183 A1 | 6/2010 | Jensen et al. |
| 2010/0191100 A1 | 7/2010 | Anderson et al. |
| 2010/0228117 A1 | 9/2010 | Hartmann |
| 2011/0015637 A1 | 1/2011 | De Smedt et al. |
| 2011/0092858 A1 * | 4/2011 | Burger ................... A61B 34/10 600/587 |

FOREIGN PATENT DOCUMENTS

| | | |
|---|---|---|
| WO | WO-2008021224 A1 | 2/2008 |
| WO | WO-2011136988 A1 | 11/2011 |

OTHER PUBLICATIONS

"CD Horizon® LEGACY™ 5.5 Spinal System—Degenerative Surgical Technique," brochure. G4 Technology Reverse-Angle Thread Form. Medtronic Sofamor Danek (2004) pp. 1-36.
"Mayfield® Skull Clamps and Headrest Systems," Mayfield® Surgical Devices Product Index, pp. 1-6, Dec. 2004 Integra LifeSciences Corporation.
"Medtronic O-Arm Multi-Dimensional Surgical Imaging System"; Brochure, 24pp, 2009.
"StealthStation_S7_System® Information Center in the OR," (2009) Medtronic, Inc.
"StealthStation® TRIA™ plus Treatment Guidance System," brochure, Medtronic Surgical Navigation Technologies (2004) 2 pages.
"TREON, StealthStation," brochure, Medtronic Surgical Navigation Technologies (2001) 8 pages.
International Search Report and Written Opinion mailed Jul. 12, 2011 for PCT/US2011/033121 claiming benefit of U.S. Appl. No. 12/771,576, filed Apr. 30, 2010.

* cited by examiner

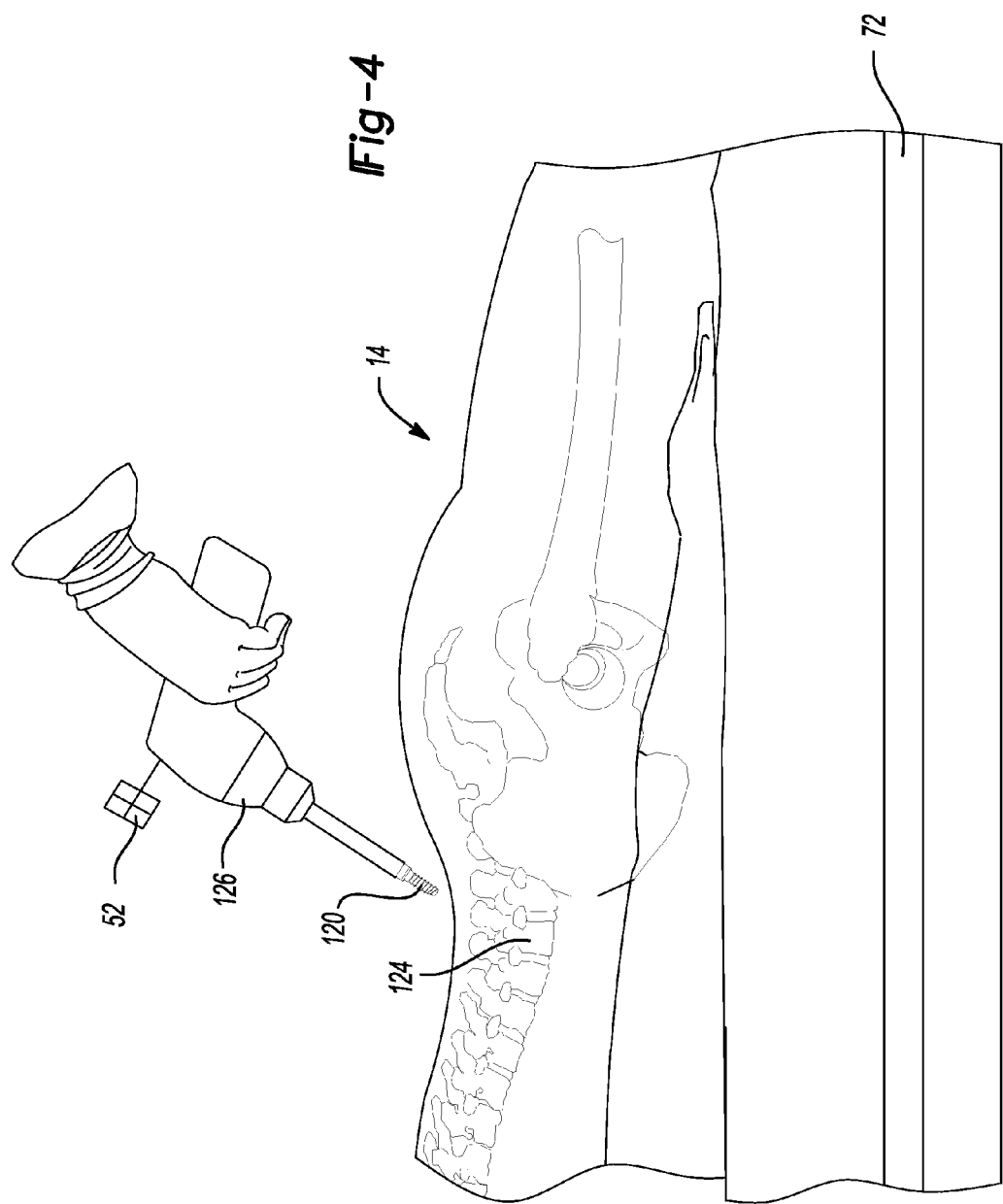

METHOD AND APPARATUS FOR IMAGE-BASED NAVIGATION

CROSS-REFERENCE TO RELATED APPLICATIONS

This application is a continuation of U.S. patent application Ser. No. 12/771,576 filed on Apr. 30, 2010. The entire disclosure of the above application is incorporated herein by reference.

FIELD

The present disclosure is directed to planning and confirming a procedure performed on a subject, and particularly to a method and system to assist in achieving a selected procedure and confirming the procedure.

BACKGROUND

This section provides background information related to the present disclosure which is not necessarily prior art.

A procedure can be performed on any appropriate subject. For example, a procedure can be performed on a patient to position an implant in the patient. Though procedures can also include assembling any appropriate work piece or installing members into a work piece, such as an airframe, autoframe, etc. Regardless of the subject, generally the procedure can have a selected result that is efficacious. The efficacious result may be the desired or best result for the procedure.

A procedure on a human patient can be a surgical procedure performed to insert an implant, such as a pedicle screw. The pedicle screw can be placed in the patient according to appropriate techniques, such as an open procedure where a surgeon can view the procedure. The surgeon can then view images of the implanted screw in the patient to analyze placement of the screw. The images acquired of the patient and the screw, however, may include artifacts due to the imaging technique and the material of the implant.

SUMMARY

This section provides a general summary of the disclosure, and is not a comprehensive disclosure of its full scope or all of its features.

A system is provided that can be used to confirm or determine a position of an implant. During a procedure, such as a surgical procedure, an implant or member can be placed in a subject. After the procedure is complete, an image can be acquired of the subject. A pre-formed model (such as a computer aided or assisted design (CAD) model) can be overlayed or superimposed on the acquired image data at the determined location of the implanted member to confirm placement of the implant. The overlayed image can be used to confirm completion of a planned procedure as well.

According to various embodiments, a surgical procedure can be performed with a navigation system. During a navigated procedure an instrument, such as a surgical instrument or implant, can be tracked relative to a patient. A planning procedure or system can also be provided and used that can illustrate and/or determine a procedure to be performed on a patient. In addition, a planning module can include a system that can execute instructions to illustrate and determine a procedure for achieving a result in a patient. A database storage system can be used to save and accumulate preferred portions of a procedure, such as entry points and trajectories.

In addition, image data can be acquired of the patient prior to implantation and subsequent to implantation, both of which can be either intra-, pre-, and post-operatively acquired, to assist in confirming placement of an implant. For example, as discussed further herein, pedicle screws can be placed in one or more vertebra of a patient. The placement of the pedicle screws can be confirmed or checked with the use of image data acquired of the patient. Further, computer aided or assisted design (CAD) models can be used to assist in viewing a placement of implants relative to the patient.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is an illustration of a detail of an instrument for inserting an implant into a patient;

Corresponding reference numerals indicate corresponding parts throughout the several views of the drawings.

DETAILED DESCRIPTION

Example embodiments will now be described more fully with reference to the accompanying drawings.

Figure 1:
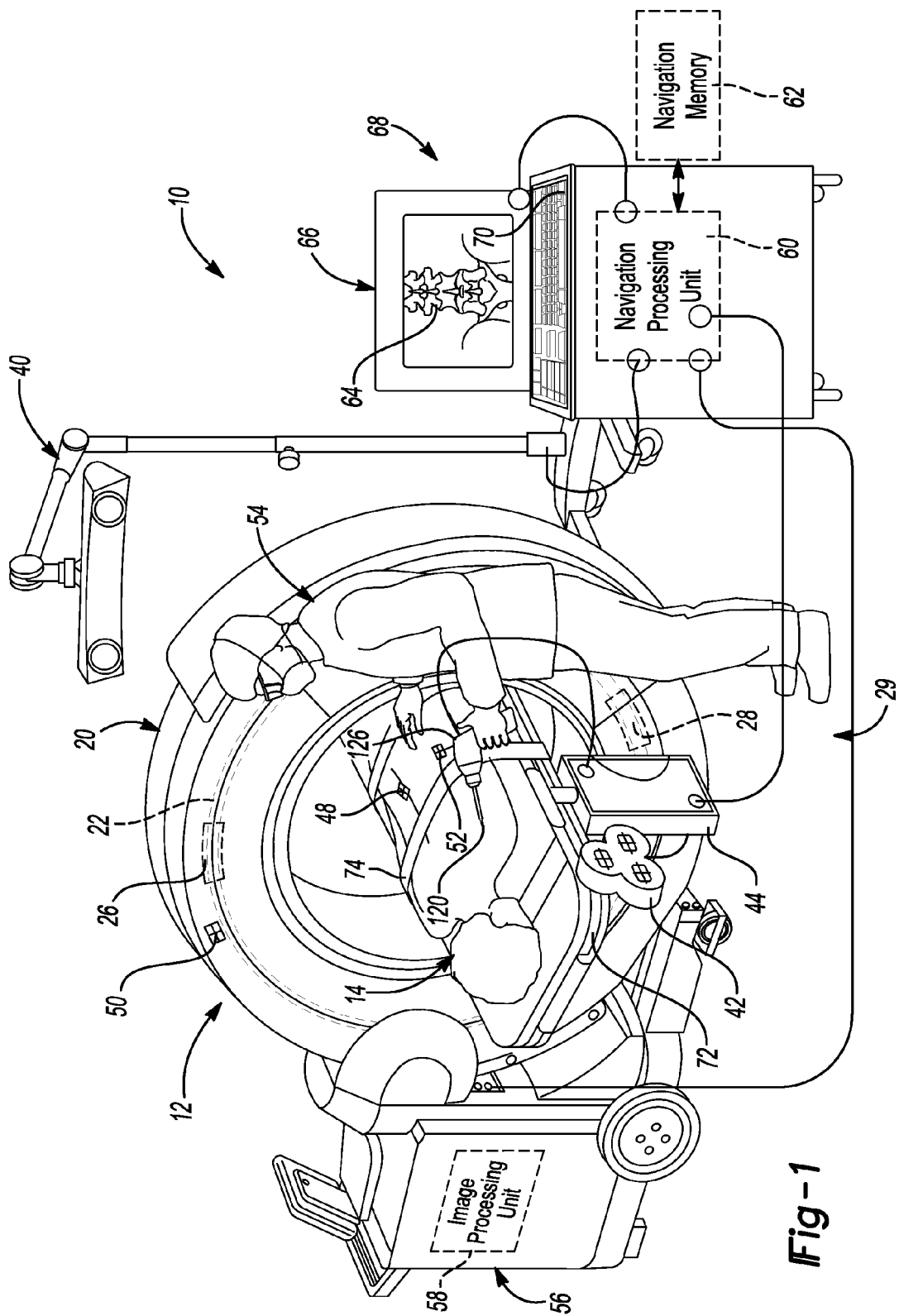
FIG. 1 is an environmental view of an operating theatre including an optional imaging system and a navigation system.
Figure 2:
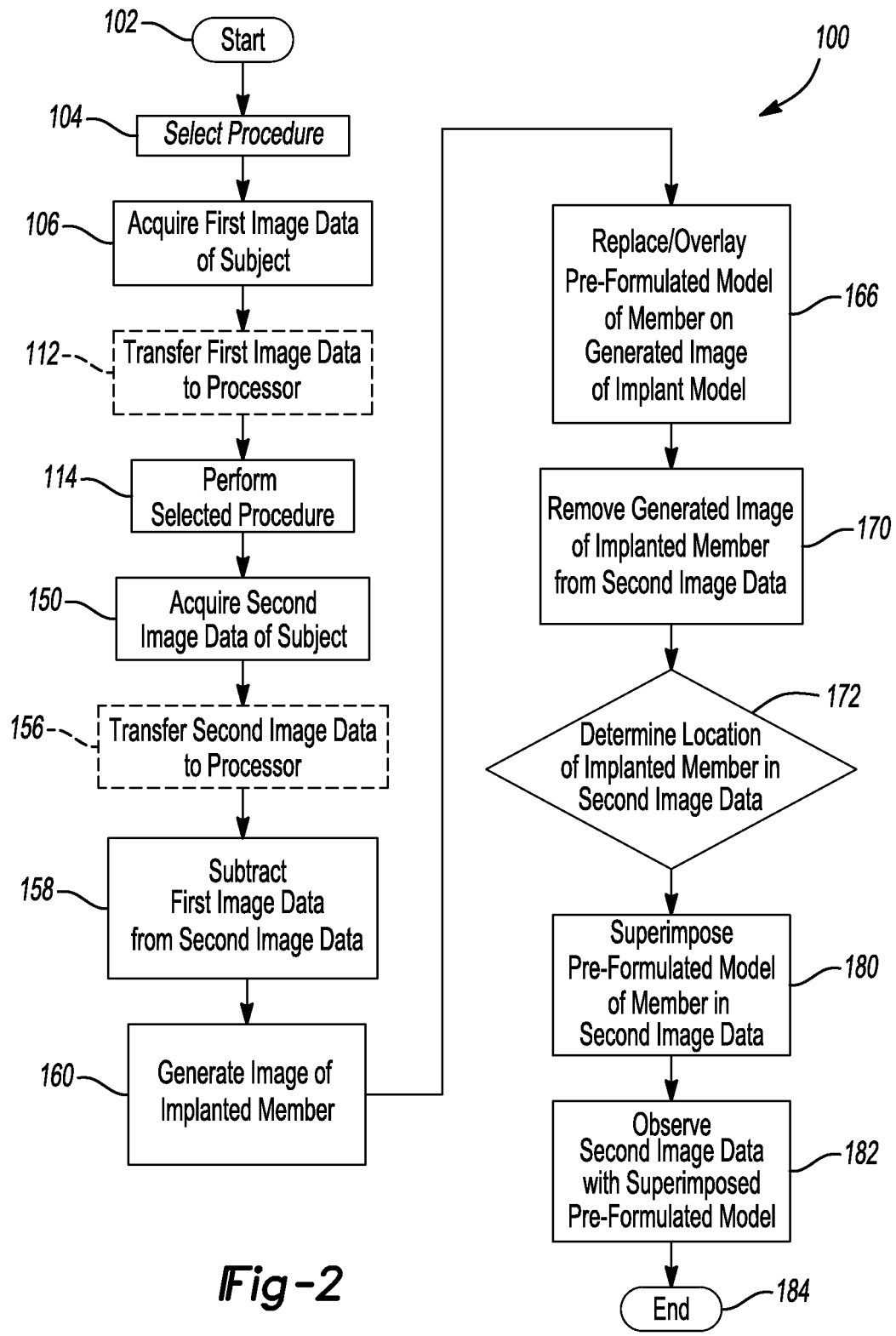
FIG. 2 is a flow chart illustrating a procedure for performing and confirming placement of an implant in a patient.

FIG. 1 is a diagram illustrating an overview of a navigation system 10 that can be used for various procedures. The navigation system 10 can be used to track the location of an item, such as an implant or an instrument (as discussed herein), relative to a subject, such as a patient 14. It should further be noted that the navigation system 10 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 10 and the various tracked items may be used in any appropriate procedure, such as one that is generally minimally invasive or an open procedure.

The navigation system 10 can interface with an imaging system 12 that is used to acquire pre-operative, intra-operative, or post-operative, or real-time image data of the patient 14. It will be understood, however, that any appropriate subject can be imaged and any appropriate procedure may be performed relative to the subject. In the example shown, the imaging system 12 comprises an O-arm® imaging device sold by Medtronic Navigation, Inc. having a place of business in Louisville, Colo., USA. The imaging device 12 may have a generally annular gantry housing 20 that encloses an image capturing portion 22. The image capturing portion 22 may include an x-ray source or emission portion 26 and an x-ray receiving or image receiving portion 28 located generally or as practically possible 180 degrees from each other and mounted on a rotor (not illustrated) relative to a track of the image capturing portion 22. The image capturing portion 22 can be operable to rotate 360 degrees during image acquisition. The image capturing portion 22 may rotate around a central point or axis, allowing image data of the patient 14 to be acquired from multiple directions or in multiple planes. The imaging system 12 can include those disclosed in U.S. Pat. Nos. 7,188,998; 7,108,421; 7,106,825; 7,001,045; and 6,940,941; all of which are incorporated by reference. Other possible imaging systems can include C-arm fluoroscopic imaging systems which can also generate three-dimensional views of the patient 14.

The position of the image capturing portion 22 can be precisely known relative to any other portion of the imaging device 12. In addition, as discussed herein, the precise knowledge of the position of the image capturing portion 22 can be used in conjunction with a tracking system 29 to determine the position of the image capturing portion 22 and the image data relative to the tracked subject, such as the patient 14.

The tracking system 29 can include various portions that are associated or included with the navigation system 10. The tracking system 29 can also include a plurality of types of tracking systems including an optical tracking system that includes an optical localizer 40 and/or an EM tracking system that can include an EM localizer 42. Various tracking devices, including those discussed further herein, can be tracked with the tracking system 29 and the information can be used by the navigation system 10 to allow for a display of a position of an item. Briefly, tracking devices, such as a patient tracking device 48, an imaging device tracking device 50, and an instrument tracking device 52, allow selected portions of the operating theater to be tracked relative to one another with the appropriate tracking system, including the optical localizer 40 and/or the EM localizer 42.

It will be understood that any of the tracking devices 48-52 can be optical or EM tracking devices, or both, depending upon the tracking localizer used to track the respective tracking devices. It will be further understood that any appropriate tracking system can be used with the navigation system 10. Alterative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. patent application Ser. No. 10/941,782, filed Sep. 15, 2004, and entitled "METHOD AND APPARATUS FOR SURGICAL NAVIGATION"; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all herein incorporated by reference.

Further, for EM tracking systems it may be necessary to provide shielding or distortion compensation systems to shield or compensate for distortions in the EM field generated by the EM localizer 42. Exemplary shielding systems include those in U.S. patent application Ser. No. 10/252,258, filed on Sep. 23, 2002, published as U.S. Pat. App. Pub. No. 2003/0117135 and U.S. Pat. No. 6,747,539, issued on Jun. 8, 2004; distortion compensation systems can include those disclosed in U.S. patent application Ser. No. 10/649,214, filed on Jan. 9, 2004, published as U.S. Pat. App. Pub. No. 2004/0116803, all of which are incorporated herein by reference.

With an EM tracking system, the localizer 42 and the various tracking devices can communicate through an EM controller 44. The EM controller can include various amplifiers, filters, electrical isolation, and other systems. The EM controller 44 can also control the coils of the localizer 42 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 44.

It will be understood that the tracking system may also be or include any appropriate tracking system, including a STEALTHSTATION® TRIA®, TREON®, and/or S7™ Navigation System having an optical localizer, similar to the optical localizer 94, sold by Medtronic Navigation, Inc. having a place of business in Louisville, Colo. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 12 can include a support housing or cart 56. The imaging system 12 can further include a separate image processing unit 58 that can be housed in the cart 56. The navigation system 10 can include the navigation processing unit 60 that can communicate or include a navigation memory 62. The navigation processing unit 60 can receive information, including image data, from the imaging system 12 and tracking information from the tracking systems 29, including the respective tracking devices 48-52 and the localizers 40-42. Image data can be displayed as an image 64 on a display device 66 of a workstation or other computer system 68. The workstation 68 can include appropriate input devices, such as a keyboard 70. It will be understood that other appropriate input devices can be included, such as a mouse, a foot pedal or the like.

The image processing unit 58 processes image data from the imaging system 12 and transmits it to the navigation processor 60. It will be further understood, however, that the imaging system 12 need not perform any image processing and it can transmit the image data directly to the navigation processing unit 60. Accordingly, the navigation system 10 may include or operate with a single or multiple processing centers or units that can access single or multiple memory systems based upon system design. The patient 14 can be fixed onto an operating table 72, but is not required to be fixed to the table 72. The table 72 can include a plurality of straps 74. The straps 74 can be secured around the patient 14 to fix the patient 14 relative to the table 72. Various apparatuses may be used to position the patient 14 in a static position on the operating table 72. Examples of such patient positioning devices are set forth in commonly assigned U.S. patent application Ser. No. 10/405,068 entitled "An Integrated Electromagnetic Navigation And Patient Positioning Device", filed Apr. 1, 2003 which is hereby incorporated by reference. Other known apparatuses may include a Mayfield® clamp.

Also, the position of the patient 14 relative to the imaging system 12 can be determined by the navigation system 10 with the patient tracking device 48 and the imaging system tracking device 50. Accordingly, the position of the patient 14 relative to the imaging system 12 can be determined. An exemplary imaging system, such as the O-arm® can know its position and be repositioned to the same position within about 10 microns. This allows for a substantially precise placement of the imaging system 12 and precise determination of the position of the imaging device 12. Precise positioning of the imaging portion 22 is further described in U.S. Pat. Nos. 7,188,998; 7,108,421; 7,106,825; 7,001,045; and 6,940,941; all of which are incorporated herein by reference. Subject or patient space and image space can be registered by identifying matching points or fiducial points in the patient space and related or identical points in the image space. The imaging device 12, such as the O-arm® imaging device sold by Medtronic, Inc., can be used to generate image data at a precise and known position. This can allow image data that is automatically or "inherently registered" to the patient 14 upon acquisition of the image data. Essentially, the position of the patient 14 is known precisely relative to the imaging system 12 due to the accurate positioning of the imaging system 12. This allows points in the image data to be known relative to points of the patient 14 because of the known precise location of the imaging system 12.

Alternatively, manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, incorporated herein by reference.

Once registered, the navigation system 10 with or including the imaging system 12, can be used to perform selected procedures. Selected procedures can use the image data generated or acquired with the imaging system 12. Further, the imaging system 12 can be used to acquire image data at different times relative to a procedure. As discussed herein, image data can be acquired of the patient 14 subsequent to a selected portion of a procedure for various purposes, including confirmation of the portion of the procedure.

With continuing reference to FIG. 1, the imaging system 12 can generate actual or virtual three dimensional images of the patient 14. The patient 14 can be placed relative to the imaging system 12 to allow the imaging system 12 to obtain image data of the patient 14. To generate 3D image data, the image data can be acquired from a plurality of views or positions relative to the patient 14. The 3D image data of the patient 14 can be used alone or with other information to assist in performing a procedure on the patient 14 or an appropriate subject. It will be understood, however, that any appropriate imaging system can be used, including magnetic resonance imaging, computed tomography, fluoroscopy, etc.

With reference to FIG. 2, and FIGS. 3A-8, a flow chart 100 illustrates a method for confirming placement of an implant after an implantation procedure as illustrated in FIGS. 3A-8. It will be understood that although the flowchart 100 describes and is directed to a method of placing pedicle screws 120 (FIG. 3) in a vertebra 124 (FIG. 4), the procedure can be used to confirm placement of any appropriate implant in any appropriate portion of the anatomy, such as an intramedullary (IM) rod in a long bone (e.g. a femur), a knee or hip replacement prosthesis, or any other appropriate procedure. Accordingly, the method in flowchart 100 will be understood to encompass selected procedures beyond pedicle screw placement. In addition, it will be understood that the method of the flowchart 100 can be used to confirm placement of any appropriate member in any appropriate structure. For example, placement of a member, including a spike, into a radio lucent work piece, such as a wood board, can also be confirmed with the procedure in the flowchart 100.

The method in the flowchart 100 can begin at start block 102. A procedure can then be selected in block 104. The procedure can be any appropriate procedure, such as the placement of the pedicle screw within the vertebra 124 of a patient 14. It will be understood that the placement of the pedicle screw 120 in the vertebra 124 of the patient 14 can be performed for any appropriate procedure, such as spinal fusion or vertebral rigidity. Regardless of the procedure selected in block 104, first image data of a subject can be acquired in block 106.

Figure 3A:
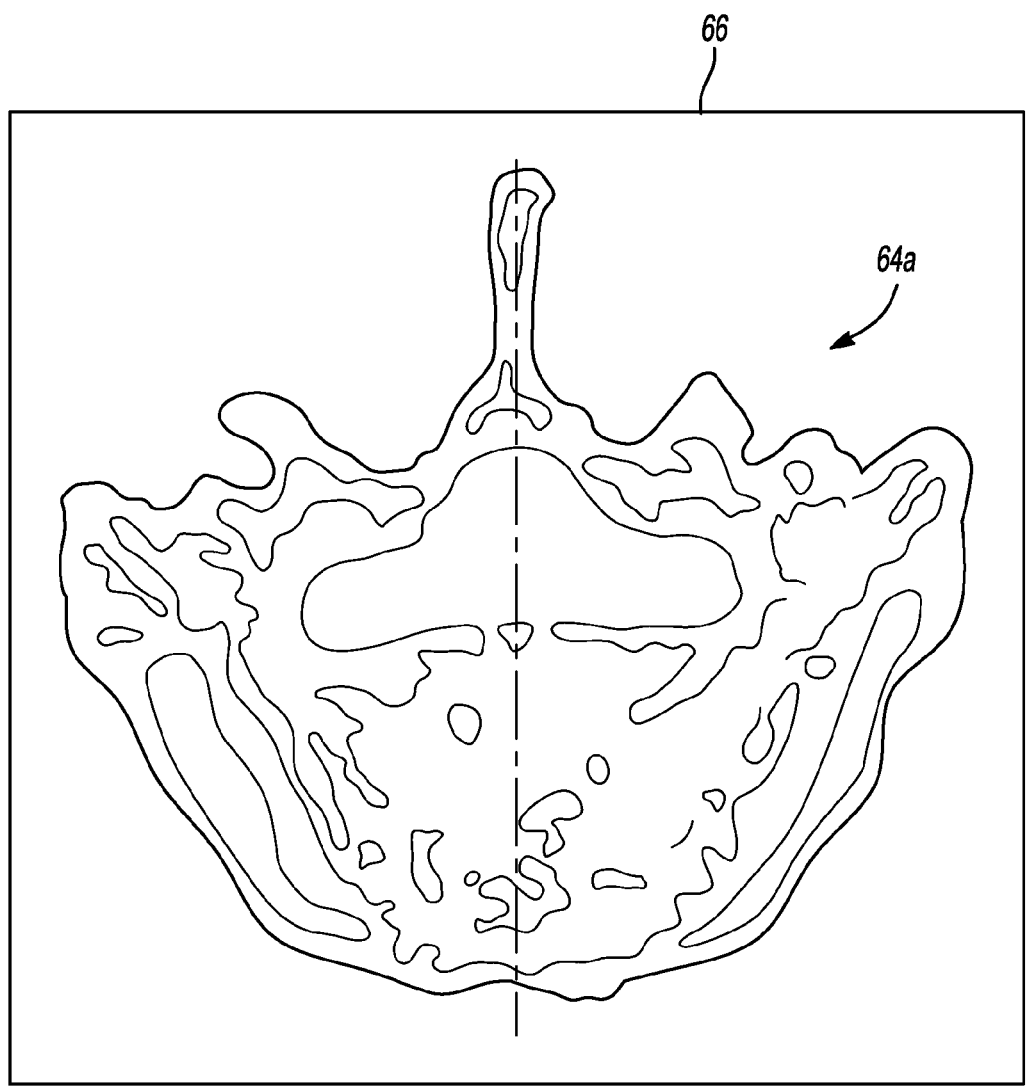
FIGS. 3A-3C illustrate image data of a spine of a patient from various perspectives.

The image data 64 can be any appropriate image data, such as x-ray image data of a single vertebra, illustrated in FIG. 3A. The image data 64 can be displayed on the display 66 or can be acquired and saved in the memory or storage system 62 of the navigation system 10, can be used for later confirmation of a procedure, or can be used for both. Briefly, a first image data of the subject can be image data acquired of the subject or the patient 14 prior to any portion of a surgical intervention being performed. For example, the patient 14 can be imaged with the imaging system 12 substantially immediately after entering an operating theatre and prior to performing any surgical procedures, such as forming an incision. It will be further understood that the first image data of the subject acquired in block 106 can be acquired prior to the patient 14 entering the surgical theatre. Regardless of the timing of acquiring the first image data, the first image data is image data of the patient or subject 14 having been unaltered by a surgical procedure. As discussed further herein, in relation to the method in the flowchart 100, this image data can be used along with later or second acquired image data and a model (e.g. a CAD model) of an implant for confirmation of placement of an implant in the patient 14. The first acquired image data can be subtracted from the second acquired image data to substantially define only the anatomy of the patient 14 that has not been affected by a surgical procedure or artifacts that may be induced by an implant member in the image data.

Figure 3B:
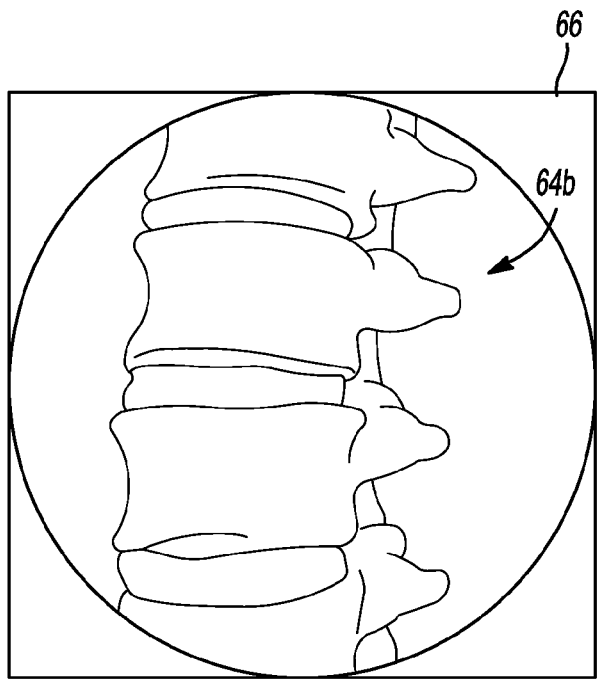
Figure 3C:
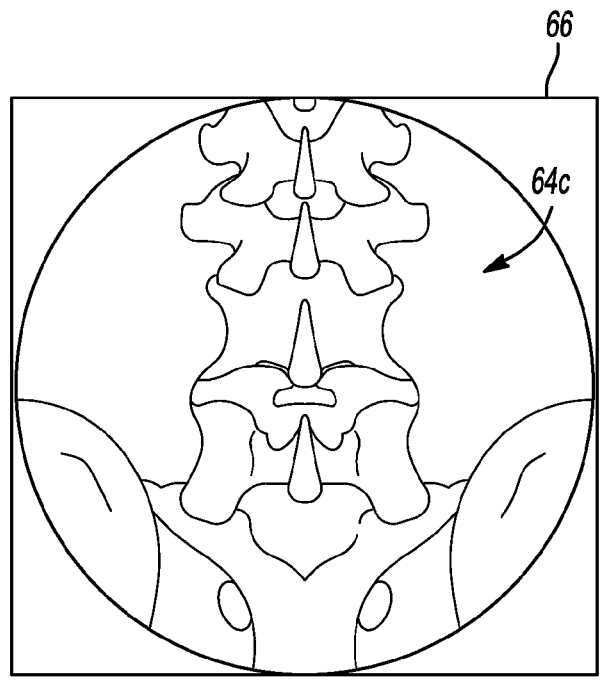

After the first image data is acquired in block 106, the first image data can be optionally transferred to a data processor in block 112. The image data transferred to the data processor in block 112 can be all first image data acquired of the patient 14 in the first image data from block 106. As illustrated in FIGS. 3A-3C, image data can be acquired of the patient 14 from a plurality of perspectives or viewpoints.

The first image data acquired in block 106 can be saved or transferred to any appropriate processing core or system, or can simply be directly transferred or maintained to be accessed by a single processing unit. As discussed above, the imaging processing unit 58 can be incorporated in the imaging system 12 and the navigation processor 60 can be included with the navigation workstation 68. Accordingly, the two processing units can communicate and image data can be transferred between. Alternatively, the image data can be simply acquired and transferred to the navigation processor 60. Regardless, it will be understood that the navigation system 10 can process the image data with a single or multiple processing unit or cores as understood by one skilled in the art.

Once the first image data is acquired in block 106 and optionally transferred to a processor in block 112, the selected procedure can be performed in block 114. As illustrated in FIG. 4, the procedure can include placement of a pedicle screw 120 into the patient 14. As is generally understood, the anatomy of the patient 14 can include a vertebra 124 into which the pedicle screw 120 can be positioned or implanted. The pedicle screw 120 can be implanted with an appropriate surgical instrument, such as a screw gun 126 or can be implanted with an appropriate manual driver (not illustrated) such as the CD Horizon® Legacy™ System manual driver, sold by Medtronic Spine and Biologics having a place of business in Minneapolis, Minn. Regardless of the instrument used to implant the pedicle screw 120, the instruments or the pedicle screw can include a tracking device 52. The tracking device 52 can be tracked by within the navigation system 10, such as with either or both of the tracking systems including the optical localizer 40 or the EM localizer 42 during the surgical procedure.

Figure 5:
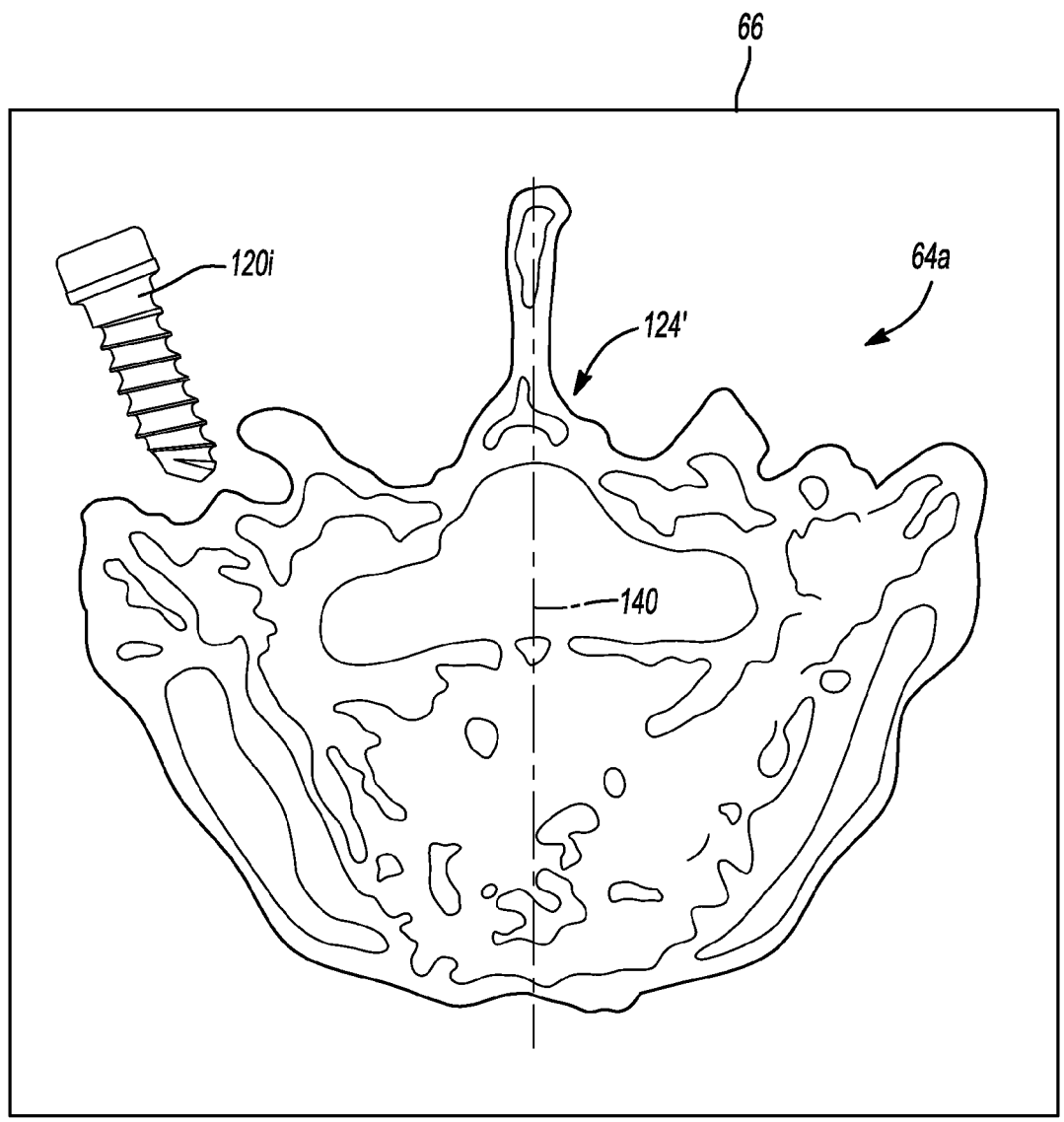
FIG. 5 is a view of a display device showing image data of a patient and an icon of an implant relative to the image data.

The tracking device 52 allows the navigation system 10 to determine and illustrate a position of the pedicle screw 120, the implantation instrument 126, or combinations thereof relative to image data acquired of the patient 14. For example, as illustrated in FIG. 5, an icon 120i can be superimposed on the first acquired image data 64a of the patient 14 as the pedicle screw 120 is moved towards the vertebra 124 of the patient 14. As illustrated in FIG. 5, as the pedicle screw 120 moves towards the vertebra 124, an icon 120i can be illustrated to move towards and into the vertebra image data 64a. The icon 120i can be a preformed CAD model of the screw including a priori precise dimension information. The preformed model can be stored in the navigation memory device 62 can be accessed by an appropriate processor, such as the navigation processor 60. It will also be understood that the image data 64a of the vertebra can include other information such as a centerline icon 140 that can be automatically or manually determined relative to the image data 64a.

The navigation system 10, by tracking the pedicle screw 120 either directly or through a navigated instrument, can be used to illustrate or determine a position of the pedicle screw 120 relative to the vertebra 124. By illustrating an icon 120i superimposed on the image data 64a of the patient 14, the user 54 can guide or be given feedback regarding the position of the pedicle screw 120 relative to the patient 14 and the vertebra 124. Accordingly, at a selected time, the user can select to stop driving the pedicle screw 120 into the patient's 14 vertebra 124 based upon the position of the icon 120i or other appropriate information.

Figure 6:
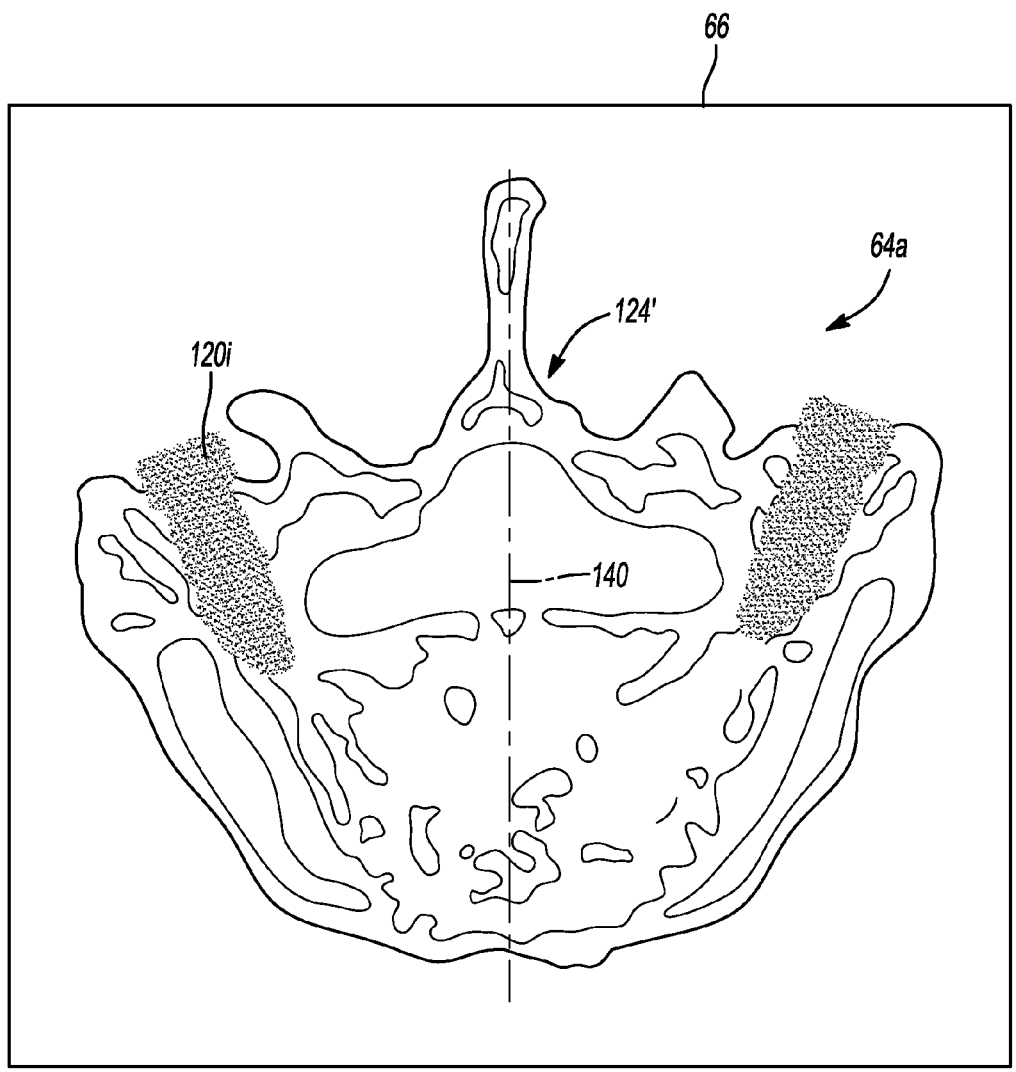
FIG. 6 is a display illustrating image data of a portion of patient with an implant implanted.

Once the user 54 determines to stop driving the pedicle screw 120 into the vertebra 124, second image data 154 of the subject can be acquired in block 150. The second image data acquired of the patient 14 in block 150 can be image data that is acquired with the imaging system 12, or any appropriate imaging system, of the patient 14 after the pedicle screw 120 is positioned within the vertebra 124. As illustrated in FIG. 6, the second image data of the vertebra 124 can include image data of the vertebra 124' and image data of one or more pedicle screws 120'. The image data of the pedicle screws 120' can be or may be distorted or include artifacts due to the type of imaging modality used by the imaging system 12. For example, the pedicle screw 120 can be formed of a metal which can generate artifacts in x-ray image data acquired of the patient 14. The artifacts can generate a fuzzy or distorted image of the true dimensions of the pedicle screw 120 in the second acquired image data.

After the second image data has been acquired of the patient 14 in block 150, the image data can be displayed as a second image 154 on the display 66, as illustrated in FIG. 6, and/or transferred to in the appropriate processor (e.g. the imaging processor 58 or the navigation processor 60) block 156 of the flowchart 100. It will be understood, as discussed above, that transferring the image data to a second image data processor is not required. Rather the second image data can also be processed in the processing unit 58 of the imaging system 12 or in the navigation processing unit 60, or in any appropriate processing unit. As discussed above, the inclusion of multiple processors can be used to speed processing and specialization of processing tasks. It will be understood, however, that a single processor can execute various program modules to process image data, navigate, track instruments, and track devices and the like. Accordingly, including more than one processing unit is not a requirement.

The second image data, which can be referred to herein by the second image 154 formed by the second image data, can be compared or subtracted from the first image data, which can be referred to herein by the first image 64a-c formed by the image data. As illustrated in FIG. 6, the second image data 154 can include image data of both the vertebra 124, such as an x-ray image 124', and can also include image data of the pedicle screw 120, as pedicle screw shadows 120'. It will be understood that more than one pedicle screw can be implanted into a single vertebra for a single procedure. According to various embodiments, the imaging device 12 can cause artifacts in the image data 154 after the implant 120 is positioned within the anatomy of the patient 14.

As illustrated schematically in FIG. 6, the shadows of the pedicle screws 120' are indistinct or lack sharp edges. The fuzziness can be caused due to artifacts in the imaging process of the implants 120, via processing artifacts, or other imaging issues with imaging the implants 120. Regardless, the second image data 154 that includes image data relating to the implants 120 that have an implant into the patient 14 while performing the selected procedure in block 114 can lead to an imprecise determination of position of the implants 120 in the patient 14 with the second image data 154.

Subtraction of the first image data from the second image data in block 158 can be performed to identify or eliminate from the second image data 154 substantially all of the second image data 154 that is not related to the implants 120 in the vertebra 124. Also, tracking information and a priori information regarding the dimensions of the implant or interaction of the implant can be used to determine more precisely the position of the screws 120. A priori information can include precise screw or other implant dimensions, including width, length, etc. A priori information can include interactions such as dilation of the anatomy from the screw, etc.

The screws are tracked relative to the patient 14 that has been registered to the image data 64, 154, as discussed above. Thus, a position of the screw 120 can be determined in the image data 154 based on the tracked position of the screw 120. The dimensions of the screw 120, based on the a priori information in the CAD model (or other model information) can be used with the determined location to assist in determining the position of the screw 120' in the second image data 154. This can also help with the subtraction, as discussed herein.

Figure 7:
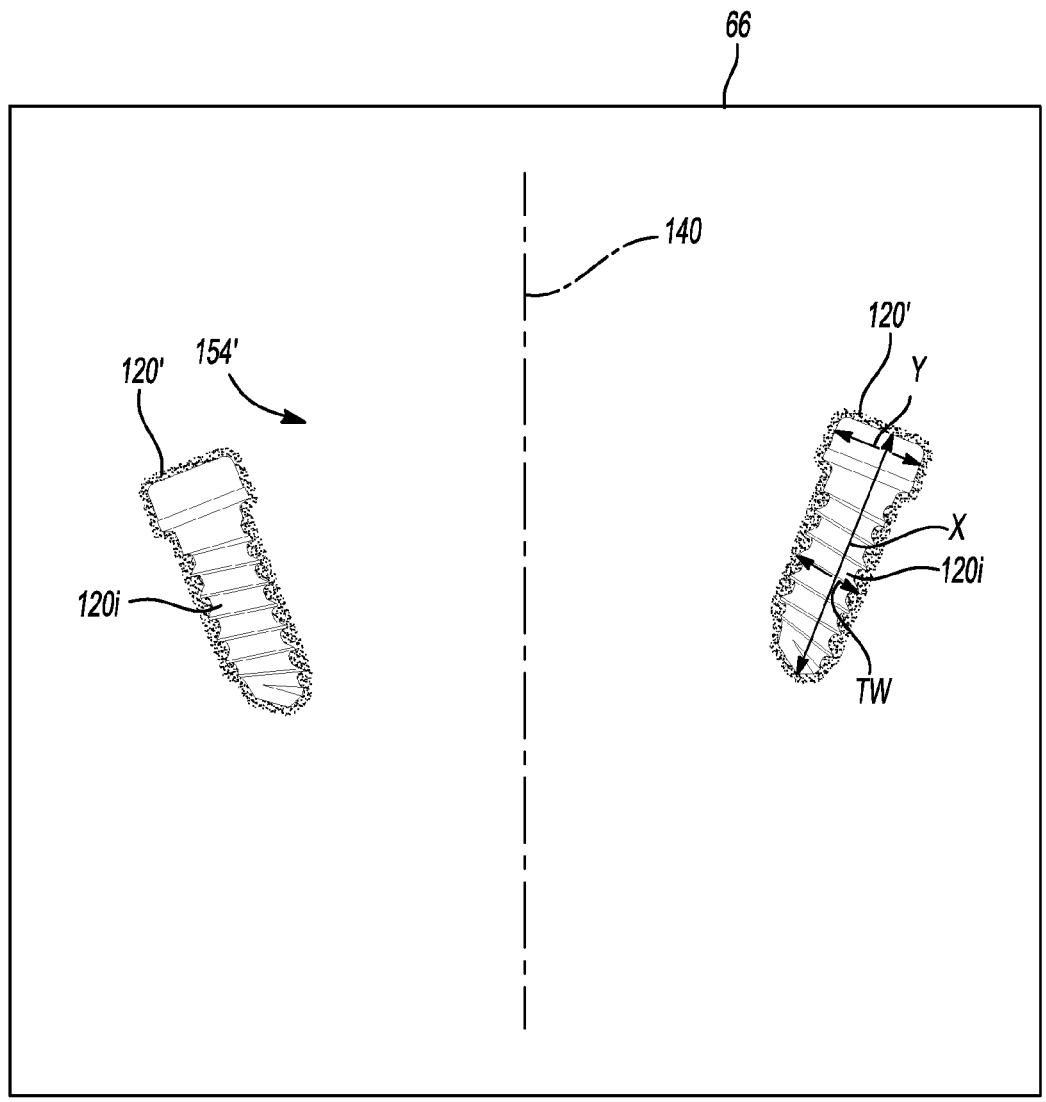
FIG. 7 is a view of a display with an augmented image data with a model superimposed on implant image data.
Figure 8:
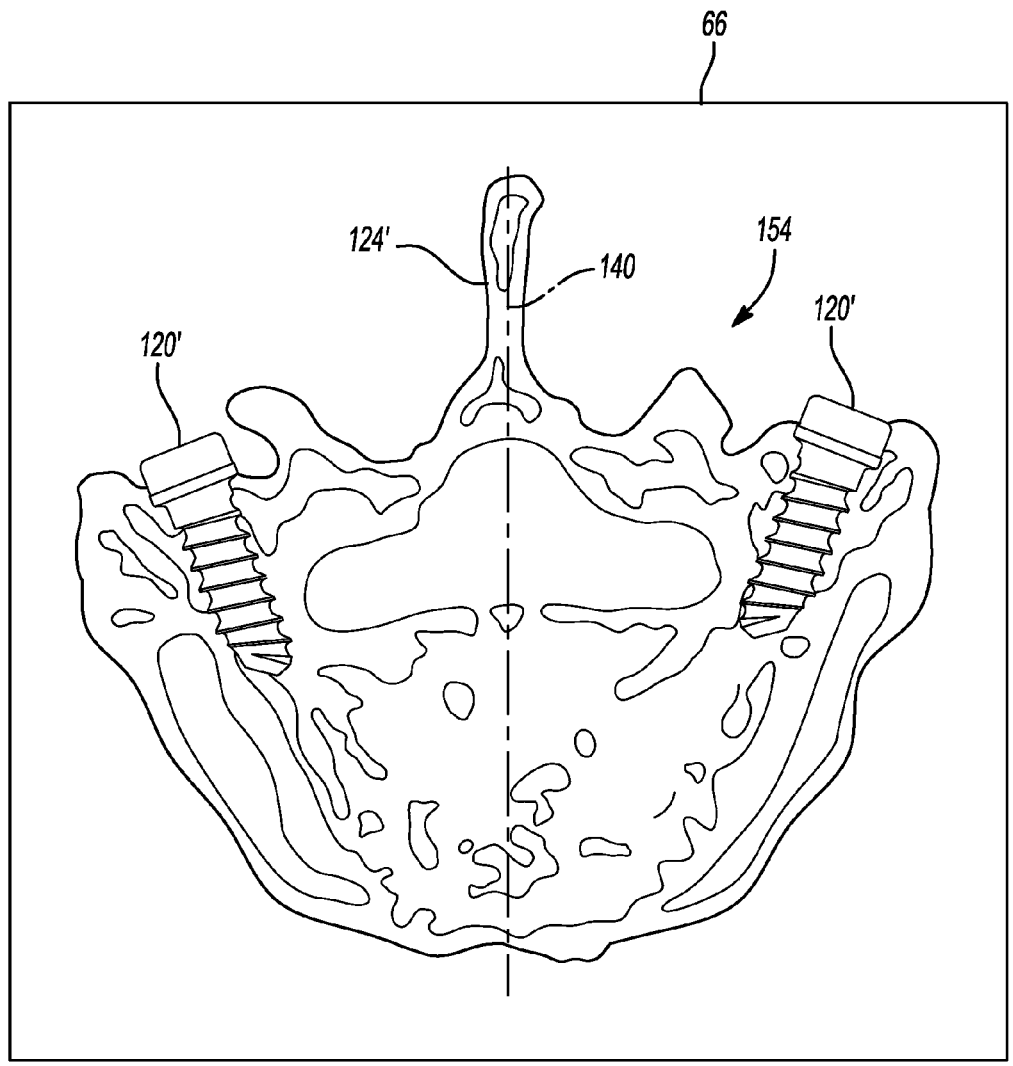
FIG. 8 is a view of a display with image data and model of an implant superimposed on the image data.

As illustrated in FIG. 7, subtraction of the anatomical image data included in the first image data 64 can be used to generate augmented second image data of the implanted member in block 160. The generated augmented second image data of the implant, as illustrated in FIG. 7, can include image data which only occurs in the second image data 154 after the procedure is performed. Generally, the first image data 64 can be subtracted from the second image data 154 to generate the augmented image data 154'. In addition, the a priori information can be used to assist in the subtraction of the second image data that does not occur due to the implant image 120'.

The generated augmented second image of the implanted member in block 160 can generate augmented second image data 154'. The augmented second image data 154' can include substantially only the image data as it relates to the placement or is caused by the implants 120 positioned in the patient 14. In the augmented second image data 154', the shadows of the implants 120' can be illustrated on the display 66, either alone or with other icons, as discussed further herein.

In addition, the generation of the augmented second image data of the implanted member in block 160 can also be generated using information relating to the navigation (including location and orientation, sometimes referred together as position) of the implants 120 into the vertebra 124. As discussed above, the instrument 126 can be tracked as the procedure is performed. The position of the screws 120 can be illustrated relative to the first image data 64, as illustrated in FIG. 5 where the pedicle screw icon 120i is shown relative to the vertebra image 124'. The position of the pedicle screw 120 can therefore be determined, via tracking the screw 120 with the tracking device 52, relative to the patient 14. As discussed above, the patient 14 can be registered to the image data 64 and tracked with the patient tracking device 48. In addition, various landmarks, such as the centerline 140, can be determined relative to the tracked position of the pedicle screws. Accordingly, the position of the pedicle screw 120 that is tracked relative to the patient 14 can also be used in identifying and determining the portion of the second image data 154 that substantially defines the pedicle screw 120 alone. Moreover, the known or a priori structure of the pedicle screw 120 can be inputted into the system, such as the navigation system 10, and further be used to identify the portion of the second image data 154 that is the pedicle screw 120. For example, a pedicle screw can be known to have a selected length X maximum width Y and a thread width TW that can also be used to identify the portion of the second image data that relates to the pedicle screw 120. The dimensions of the screw 120 can be part of a pre-formed model (e.g. a CAD model) including a priori dimension information of the screw 120.

All of the information, including the tracking data, the dimensions of the pedicle screw 120, and the subtraction of the first image data 64 can be used to generate the augmented second image data 154'. Once the augmented second image data 154' has been generated in block 160, the portion of the image data that is the pedicle screw 120' can be overlaid or replaced with the pre-formed or CAD model of the implanted member in block 166. The CAD model can include or be the icon 120i of the screw being implanted that is overlaid substantially on the augmented second image data 154' that identifies the implanted positions of the screws 120. The CAD model can include the precise dimensions of the implanted member 120 and can be overlaid on the augmented image data 154' at the positions identified as the area relating to the implants 120. It will be understood that the image data 64, the second image data 154, and the augmented image data 154' can all be two dimensional and/or three dimensional data. Further, the icons 120i can also include three dimensional structures or information and can be overlaid in orientation and location relative to the acquired image data 154' and landmarks therein, such as the centerline 140. Therefore, the icons 124i can be overlaid at the determined position of the implanted members 120 in the image data.

After the CAD representation of the implants 120i has been overlaid or positioned at the identified position of the implants in block 166, the augmented or generated second image data 154' can be removed in block 170 leaving substantially only the icons 120i representing the CAD models. A determination of the position of the implanted member can be made in block 172 which can include the tracked information regarding the implanted implants 120, the augmented image data 154', and other information. The position of the implants can be used for confirmation, as discussed below.

Once the overlaid or determined position of the icons 120i' is determined, they can be superimposed onto the second image data 154 and displayed on the display 66 in block 180. The user 54 can then observe the second image data with the superimposed icons in block 182. The second image data 154, as discussed above, is acquired after the implantation of the implant 120 has occurred. Accordingly, the second image data 154 is a substantially concurrent or current image of the patient 14. Therefore, having the icons 120i superimposed on the second image data 154 can provide a substantially clear indication to the user 54 of the precise location of the implanted members 120 in the vertebra 124. Because the position of the implants 120 was determined substantially precisely via the image subtraction, the tracking information, and other information, the icons 120i are superimposed on the second image data 154 at substantially the precise location where they are implanted in the patient 14. The icons 120i, however, do not suffer from any artifacts or blurring due to imaging artifacts of the implants 120. Accordingly, the icons 120i provide a substantially precise and clear image to the user 54 of the position of the implants 120 in the vertebra 124.

The position of the implants 120 in the vertebra 124 can be confirmed to ensure non-perforation and proper placement of the implants 120 in the vertebra 124. Perforation of a vertebra by the implant 120 may be undesirable for various purposes known to one skilled in the art. Thus, the icons 120i can be used by the user 54 to ensure that a procedure has occurred according to the plan of the user 54 or according to preferences of the user 54. The confirmation procedure can then end in block 184.

The confirmation procedure can be used to assist in determining that a selected procedure has occurred or that an implant has been positioned in the patient 14 as selected by the user 54. According to various embodiments, a procedure can be planned based upon a pre-planned or generated planned procedure that can include inputs and substantially automatically generate a plan for a selected procedure, such as positioning the pedicle screw 120 into the vertebra 124.

Figure 9:
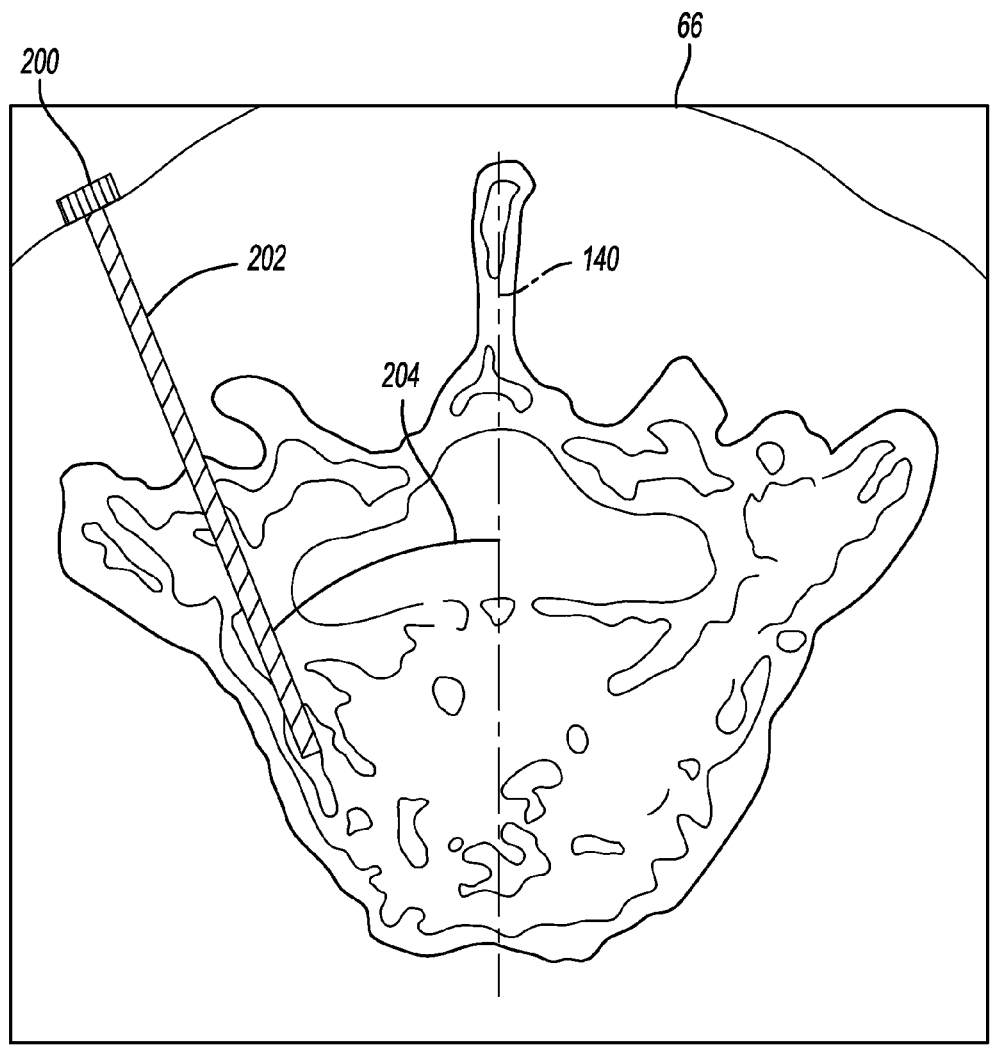
FIG. 9 is a view of a display showing a plan for a procedure.

A program or algorithm can be executed based upon various inputs to identify a plan for achieving or performing a selected procedure. For example, as illustrated in FIG. 9, an algorithm can be used to identify a proposed entry point 200, a proposed path of implantation 202, the centerline or other anatomical feature of the vertebra 140, an angle 204 relative to the centerline 140, selected implant for implantation (e.g. specific dimension, model, etc.), and other appropriate features of a planned procedure. The proposed entry point 200 and the proposed path of implantation 202 can be maintained or input as a planned entry point 200 and a planned path of implantation 202. The proposed entry point 200 and the proposed path of implantation 202 can become planned based on agreement by the user 54, such as a surgeon or automatically. Additionally, the algorithm can be executed by a processor automatically based on a plurality of saved instructions that can be saved on an appropriate storage device or medium.

The plan, as illustrated on the display 66, can be based upon preferences from the user 54. For example, the algorithm can include accessing a database of preferences of the user 54, such as preferred instrumentation, preferred implant models, preferred entry points, preferred angles, and other appropriate user preferences. The user preferences can be accessed by the algorithm to identify an appropriate or preferred entry point 200 for the user 54 for the specific patient 14. For example, the user 54 may prefer to have an entry angle 204 of about 10 degrees. The database accessed by the algorithm can access the user preferences of having the approximately 10 degree entry angle and identify entry points 200 and trajectories to achieve the preferred entry angle. Accordingly, the algorithm can identify and assist in planning a procedure.

Preferences of the user 54 can be input or generated in a selected manner. For example, prior to a procedure the user 54 can input user preferences, such as selecting an implant, entry point, etc. The user 54 may be presented with a form and enter in the appropriate information on the form. The form may be on a monitor (to allow the user 54 to input the preferences directly) or the form can be written and the preferences can be entered by an appropriate data entry person.

Preferences of the user 54 can also be stored or "generated" by the planning algorithm. A procedure may be performed by the user 54 and the selected implants, entry point, angle and/or path of implantation, and other parameters can be stored by the memory device. The processor executing the planning algorithm can then access the memory device and retrieve the parameters of one or more previous similar or identical procedures. As more procedures are completed by the user 54 the planning algorithm can better predict or select proposed and/or planned entry points, implants, and other parameters for a new or subsequent procedure performed by the user 54. Additionally, a plurality of users can access the same database of past procedures so that plans need not be based on only the experiences of one user.

The pre-planned procedure can also be used to assist in confirming placement of the implant 120 in the vertebra 124. The confirmation can be used to ensure that the planned procedure has occurred and the implant, such as the pedicle screw 120, has been positioned in the planned position. For example, the user 54 can select or generate a plan based upon preferred and optimal positioning. The second image data 154 with the superimposed models can be compared to the generated plan for confirmation.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system for use with a procedure, comprising:
a first communication system configured to communicate a first image data of a volume prior to performing the procedure;
a second communication system configured to communicate a second image data of the volume subsequent to performing the procedure that includes positioning a member in the volume;
a memory system configured to store a pre-formed model of the member, wherein the model includes exterior dimensions of the member;
a processor system associated with the first communication system and the second communication system, wherein the processor is configured to:
compare the first communicated image data and the second communicated image data by at least subtracting the first communicated image data from the second communicated image data based at least on a tracked location of the member, wherein the second image data is acquired after the member is placed in the volume and the member distorts the volume and/or causes artifacts in the second image data;
generate an augmented image to compensate for at least distortion or artifacts in the second communicated image data based on the (i) subtracted first communicated image data from the second communicated image data and (ii) accounting for the member based on a priori information of the member in the pre-formed model of the member including at least one of possible distortion or artifacts in the communicated second image data based on a priori information of possible artifacts caused by interference of a material and/or a characteristic of the member caused by an imaging modality to acquire the second image data; and
determine a real time true position of the member positioned in the volume during the selected procedure in the second communicated image data based at least on the augmented image;
superimpose the pre-formed model of the member on the second communicated image data at the determined real time true position of the member.

2. The system of claim 1, wherein the processor is further configured to compensate for at least the distortion or artifacts of the communicated second image data subsequent to implanting the member.

3. The system of claim 2, wherein the distortion or artifacts are caused at least by interaction of the member with an anatomy of a subject in the volume or interaction of the member with an imaging system that acquired the first communicated image data or the second communicated image data and the determined real time true position is based at least on a recalled a priori interaction of the member with the anatomy of the subject in the volume at the location of the implanted member in the anatomy of the subject.

4. The system of claim 1, further comprising:
a display device configured to display the second communicated image data and the pre-formed model of the member on the second communicated image data at the determined real time true position.

5. The system of claim 1, wherein the pre-formed model of the member includes stored substantially precise dimensions of the member including length, width, thread pitch, taper angle, and combinations thereof.

6. The system of claim 1, wherein the memory system further includes a priori information relating to an interaction of the member with the volume;
wherein the determined real time true position of the member includes incorporating a called a priori information of interaction of the member with the volume from the memory system including dilatation of an anatomy, screw and human anatomy interaction dynamics, and combinations thereof.

7. The system of claim 6, further comprising:
a tracking system to track a location of the member relative to the volume including at least a tracking device associated with the member;
a navigation system configured to register the first communicated image data and the second communicated image data to the volume; and
a navigation memory system configured to save the tracked position of the member relative to the volume and the registered first communicated image data and the second communicated image data; and
wherein the navigation system or the processor system is configured to compare the tracked position that is saved of the member relative to the first communicated image data to the second communicated image data.

8. The system of claim 7, wherein the determine a real time true position of the member is displayed with a display device based at least on applying a called pre-formed model of the member from the memory system and the saved tracked location of the member.

9. The system of claim 1, further comprising:
an imager system configured to acquire at least one of the first image data or the second image data;
wherein the imager system is further in communication with at least one of the first communication system or the second communication system.

10. A system for use with a procedure, comprising:
a processor system;
a memory system including a pre-formed model of a member to be positioned in a volume;
a first image transfer system to transfer a first image data of the volume to the processor system;
a second image transfer system to transfer a second image data of the volume to the processor system, wherein the second image data is acquired of the volume after the first image data and after the member is placed in the volume, wherein the member distorts the volume and/or causes artifacts in the second image data; and
a display to display a generated image data based on a subtraction of the first image data from the second image data;
wherein the processor system is configured to:
call from the memory system the pre-formed model of the member,
refine the generated image data to determine a position and a dimension of the member in the volume at least by comparing the called pre-formed model of the member including at least possible at least one of distortion or artifacts in second image data of the member based on a tracked location of the member to correct for the at least one of distortion or artifacts caused by the member placed in the volume in the second image data and based at least on known artefacts caused by interference of a material and/or a characteristic of the member caused by an imaging modality during acquiring the second image data,
determine a true real time location of the member in the second image data, and
overlay the pre-formed model on the generated image data at the true real time location of the member in the volume.

11. The system of claim 10, further comprising:
a tracking system to track the member relative to the volume to determine the tracked location of the member.

12. The system of claim 10, wherein the memory system includes a priori information regarding a real time interaction of the member with the volume;
wherein the generated image data is further refined based on the a priori information regarding the real time interaction of the member with the volume.

13. The system of claim 12, wherein the volume includes a volume of a human subject.

14. The system of claim 13, further comprising:
the processor system further configured to determine a location of the member in the second image data and replace the member in the second image data with the pre-formed model of the member at the determined location of the member.

15. The system of claim 14, wherein the display device is further configured to display the pre-formed model of the member at the determined location of the member in the second image data.

16. The system of claim 15, wherein the processor is configured to generate a displayable image including substantially only the second image data and the superimposed pre-formed model member and the display device is configured to display the displayable image.

17. The system of claim 10, further comprising:
an imager system configured to acquire at least one of the first image data or the second image data;
wherein at least one of the first image transfer system or the second image transfer system transfers at least one of the first image data or the second image data from the imager system.

18. A system for use with a procedure, comprising:
an imager system configured to acquire at least one of a first image data of a volume and having a first image space or a second image data of the volume having a second image space, wherein the second image data is acquired after the first image data;
a processor system;
a memory system including a pre-formed model of a member to be positioned in a volume having a volume space;
a first image transfer system to transfer the first image data of the volume to the processor system;
a second image transfer system to transfer the second image data of the volume to the processor system;
a tracking system to track the member relative to the volume to determine a tracked location of the member in the second image space of the second image data; and
a display to display a generated image data based on a subtraction of the first image data from the second image data to compensate for distortion due at least to the member implanted in the volume;

wherein the second image data is acquired after the member is placed in the volume and the member distorts the volume and/or causes artifacts in the second image data;

wherein the processor system is configured to:

call from the memory system the pre-formed model of the member including at least exterior dimensions of the member;

compare the first image data and the second image data by at least subtracting the first image data from the second image data based at least on the determined tracked location of the member;

generate an augmented image to compensate for at least one of the distortion or the artifacts in the second image data based on (i) the subtracted first image data from the second image data and (ii) accounting for the member based on a priori information of the member in the pre-formed model of the member including at least possible at least one of distortion or artefacts in the second image data based at least on known artefacts caused by interference of a material and/or a characteristic of the member caused by an imaging modality to acquire the second image data;

determine a real time true position of the member positioned in the volume in the second image data based at least on the augmented image; and overlay the pre-formed model on the second image data at the determined real time true position of the member in the volume based at least on the generated augmented image data.

* * * * *